US008765690B2

(12) United States Patent
Handisides et al.

(10) Patent No.: US 8,765,690 B2
(45) Date of Patent: Jul. 1, 2014

(54) TREATMENT OF CANCER WITH GLUFOSFAMIDE IN PATIENTS NOT RECEIVING INSULIN THERAPY

(75) Inventors: Damian Handisides, San Carlos, CA (US); Stewart Kroll, Oakland, CA (US); Jian-Xin Duan, South San Francisco, CA (US); Harold E. Selick, Belmont, CA (US)

(73) Assignee: Threshold Pharmaceuticals, Inc., South San Francisco, CA (US)

( * ) Notice: Subject to any disclaimer, the term of this patent is extended or adjusted under 35 U.S.C. 154(b) by 793 days.

(21) Appl. No.: 12/594,802

(22) PCT Filed: Apr. 7, 2008

(86) PCT No.: PCT/US2008/059578
§ 371 (c)(1),
(2), (4) Date: Jan. 8, 2010

(87) PCT Pub. No.: WO2008/124691
PCT Pub. Date: Oct. 16, 2008

(65) Prior Publication Data
US 2010/0104549 A1     Apr. 29, 2010

Related U.S. Application Data

(60) Provisional application No. 60/991,660, filed on Nov. 30, 2007, provisional application No. 60/952,686, filed on Jul. 30, 2007, provisional application No. 60/915,882, filed on May 3, 2007, provisional application No. 60/910,403, filed on Apr. 5, 2007.

(51) Int. Cl.
*A61K 31/70* (2006.01)

(52) U.S. Cl.
USPC .......................................................... 514/25

(58) Field of Classification Search
CPC .................................................... A61K 31/70
See application file for complete search history.

(56) References Cited

U.S. PATENT DOCUMENTS

| | | | |
|---|---|---|---|
| 4,537,883 A | 8/1985 | Alexander et al. | |
| 4,808,614 A | 2/1989 | Hertel | |
| 5,464,826 A | 11/1995 | Grindey et al. | |
| 5,622,936 A | 4/1997 | Wiessler et al. | |
| 6,284,277 B1 | 9/2001 | Bouloumie et al. | |
| 6,475,486 B1 | 11/2002 | Kolar et al. | |
| 6,489,302 B1 | 12/2002 | Wiessler et al. | |
| 6,852,738 B2 | 2/2005 | Jones et al. | |
| 6,979,675 B2 | 12/2005 | Tidmarsh | |
| 7,001,888 B2 * | 2/2006 | Tidmarsh et al. | 514/23 |
| 7,560,230 B2 | 7/2009 | Tidmarsh | |
| 2004/0167079 A1 | 8/2004 | Tidmarsh | |
| 2005/0054708 A1 | 3/2005 | Michols et al. | |
| 2006/0204951 A1 | 9/2006 | Folkman et al. | |
| 2006/0258569 A1 | 11/2006 | McTavish | |
| 2006/0276527 A1 | 12/2006 | Tidmarsh | |
| 2007/0072243 A1 | 3/2007 | Meikle et al. | |
| 2009/0247480 A1 | 10/2009 | Tidmarsh | |
| 2009/0270339 A1 | 10/2009 | Li | |
| 2011/0182909 A1 | 7/2011 | Tidmarsh | |

FOREIGN PATENT DOCUMENTS

| | | |
|---|---|---|
| EP | 1711188 B1 | 10/2006 |
| WO | WO2004081181 * | 3/2004 |
| WO | WO 2005/076888 A2 | 8/2005 |
| WO | WO 2006/057946 A2 | 6/2006 |
| WO | WO 2006/071955 A2 | 7/2006 |
| WO | WO 2006/122227 A1 | 11/2006 |
| WO | WO 2007/002931 A2 | 1/2007 |
| WO | WO 2007/035961 A2 | 3/2007 |

OTHER PUBLICATIONS

Briasoulis et al., Glufosfamide administered using a 1-hour infusion given as first-line treatment for advanced pancreatic cancer. A phase II trial of the EORTC-new drug development group, 2003, Eur. J. Cancer 39: 2334-2340.*
Postic et al., Evidence for a transient inhibitory effect of insulin on GLUT2 expression in the liver: studies in vivo and in vitro, 1993, Biochem J. 293(Pt 1): 119-124.*
Burcelin et al., Evidence that GLUT-2 mRNA and protein concentrations are decreased by hyperinsulinaemia and increased by hyperglycaemia in liver of diabetic rats, 1992, Biochem J. 288(Pt 2): 675-679.*
Damyanov et al., "Low dose chemotherapy in combination with insulin for the treatment of advanced metastatic tumors. Preliminary experience.", J. Buon., Oct.-Dec. 2009, vol. 14, No. 4. [English Abstract only].
Evans et al., "Insulin as a drug of abuse in body building", Br J Sports Med, 2003, p. 356-357, vol. 37.
Holt et al., "Growth hormone, IGF-I and insulin and their abuse in sport", British Journal of Pharmacology, 2008, p. 542-556, vol. 154.
Kingsley Jones., "Insulin coma therapy in schizophrenia", Journal of the Royal Society of Medicine, Mar. 2000, p. 147-149, vol. 93.
Niazi et al., "A grand dame with hidden aces: The non-diabetic uses of insulin", Indian Journal of Endocrinology and Metabolism, 2012, p. S57-S59, vol. 16, supplement 1.
Perez et al., "Glucose-insulin-potassium (GIK) solution: cardioprotective effects of insulin", Ach. Cardiol. Mex., Oct.-Dec. 2006, pp. 144-151, vol. 76, supplement 4.
Roy et al., "Impact of Intravenous Insulin on 18F-FDG PET in Diabetic Cancer Patients", The Journal of Nuclear Medicine, Feb. 2009, p. 178-183, vol. 50, No. 2.
Zhao et al., "Effects of insulin and glucose loading on FDG uptake in experimental malignant tumors and inflammatory lesions", Eur. J. Nucl. Med., Jun. 2001, p. 730-735, vol. 28, No. 6.
U.S. Appl. No. 60/910,403, Handisides et al.

(Continued)

*Primary Examiner* — Jon P Weber
*Assistant Examiner* — Robert Yamasaki
(74) *Attorney, Agent, or Firm* — Kilpatrick Townsend & Stockton LLP (57) ABSTRACT

The co-administration of glufosfamide and a glucose lowering drug other than insulin is efficacious in cancer treatment.

10 Claims, 4 Drawing Sheets

(56) References Cited

OTHER PUBLICATIONS

International Search Report for PCT/US2008/059578, mailed Jul. 11, 2008, 2 pages.
"Cancer Drug Information", National Cancer Institute, retrieved on Oct. 6, 2011 from http://www.cancer.gov/cancertopics/druginfo/alphalist.
"Prognosis of Pancreatic Cancer", Hirshberg Foundation for Pancreatic Cancer Research, retrieved on Oct. 18, 2011 from http://www.pancreatic.org/site/c.htJYJ8MPIwE/b.891917/k.5123/Prognosis_of_. . . .
Ammons et al., "A Novel Alkylating Agent, Glufosfamide, Enhances the Activity of Gemcitabine In Vitro and In Vivo", Neoplasia, Aug. 2007, p. 625-633, vol. 9, No. 8.
Briasoulis et al., "Phase I Trial of 6-Hour Infusion of Glufosfamide, a New Alkylating Agent with Potentially Enhanced Selectivity for Tumors that Overexpress Transmembrane Glucose Transporters: A Study of the European Organization for Research and Treatment of Cancer Early Clinical Studies Group", Journal of Clinical Oncology, Oct. 15, 2000, p. 3535-3544, vol. 18, No. 20.
Burris III et al., "Improvements in Survival and Clinical Benefit with Gemcitabine as First-Line Therapy for Patients with Advanced Pancreas Cancer: A Randomized Trial", Journal of Clinical Oncology, Jun. 1997, p. 2403-2413, vol. 15, No. 6.
Chiorean, MD et al., "A Phase 2 Trial of Glufosfamide in Combination with Gemcitabine in Chemotherapy-Naïve Pancreatic Adenocarcinoma", American Journal of Clinical Oncology, Apr. 2010, p. 111-116, vol. 33, No. 2.
Ciuleanu et al., "A randomized Phase III trial of glufosfamide compared with best supportive care in metastatic pancreatic adenocarcinoma previously treated with gemcitabine", European Journal of Cancer, 2009, p. 1589-1596, vol. 45.
Di Cola et al., "Hypoglycemic Effect of Insulin-like Growth Factor-1 in Mice Lacking Insulin Receptors", The Journal of Clinical Investigation, May 1997, p. 2538-2544, vol. 99, No. 10.
Tandon et al., "Increased disaccharidase activity in human diabetics", The American Journal of Clinical Nutrition, Jun. 1975, p. 621-625, vol. 28.
Briasoulis et al., "Glufosfamide administered using a 1-hour infusion given as first-line treatment for advanced pancreatic cancer. A phase II trial of the EORTC-new drug development group", European Journal of Cancer, May 2003, p. 2334-2340, vol. 39.
Giaccone et al., "Glufosfamide administered by 1-hour infusion as a second-line treatement for advanced non-small cell lung cancer: a phase II trial of the EORTC-New Drug Development Group", European Journal of Cancer, 2004, p. 667-672, vol. 40.
Hertzberg et al., "Outpatient-based ifosfamide, carboplatin and etoposide (ICE) chemotherapy in transplant-eligible patients with non-Hodgkin's lymphoma and Hodgkin's disease", European Society for Medical Oncology, Annals of Oncology, 2003, p. i11-i16, vol. 14.
Kozuch et al., "Irinotecan Combined with Gemcitabine, 5-Fluorouracit, Leucovorin, and Cisplatin (G-FLIP) is an Effective and Noncrossresistant Treatment for Cemotherapy Refractory Metastatic Pancreatic Cancer", The Oncologist, 2001, p. 488-495, vol. 6.
Noble et al., "Gemcitabine: A Review of its Pharmacology and Clinical Potential in Non-Small Cell Lung Cancer and Pancreatic Cancer", Drugs, Adis Drug Evaluation, Sep. 1997, p. 447-472, vol. 54, No. 3.
Okada et al., "Phase I Trial of Gemcitabine in Patients with Advanced Pancreatic Cancer", Japanese Journal of Clinical Oncology, 2001, p. 7-12, vol. 31, No. 1.
Seker et al., "Mechanistic aspects of the cytotoxic activity of glufosfamide, a new tumor therapeutic agent", British Journal of Cancer, 2000, p. 629-634, vol. 82, No. 3.
Smith et al., "A Phase II/III Study Comparing Intravenous ZD9331 with Gemcitabine in Patients with Pancreatic Cancer", European Journal of Cancer, Jul. 1, 2003, p. 1377-1383, vol. 39.
Burris et al., "Assessing Clinical Benefits in the Treatment of Pancreas Cancer: Gemcitabine Compared to 5-Fluorouracil", European Journal of Cancer, 1997, vol. 33, suppl 1:S18-22.
Niculescu-Duvaz, I., "Glufosfamide (Baxter Oncology)", Current Opinion in Investigational Drugs, 2002, p. 1527-1532, vol. 3, No. 10.
Rothenberg et al., "A Phase II trial of gemcitabine in patients with 5-FU-refractory pancreas cancer", Annals of Oncology, 1996, p. 347-353, vol. 7.
Stephens, C.D., "Gemcitabine: A New Approach to Treating Pancreatic Cancer", Oncology Nursing Forum, 1998, p. 87-93, vol. 25, No. 1.
Araneo,M., et al., "Biweekly low-dose sequential gemcitabine, 5-fluorouracil, leucovorin, and cisplatin (GFP): A highly active novel therapy for metastatic adenocarcinoma of the exocrine pancreas", Cancer Investigation, 2003, p. 489-496, vol. 21, No. 4.
International Preliminary Report on Patentability for International Application No. PCT/US2008/059578, mailed on Jul. 11, 2008, 6 pages.
Holoxan [ifsofamide] datasheet. Baxter Healthcare, S.A., Apr. 8, 2004.
Declaration of Forrest H. Anthony dated Jul. 26, 2012 as filed on Aug. 8, 2012 in U.S. Appl. No. 10/588,409, now Patent No. 8,318,633, 7 pages (the "Anthony Declaration").
Appendix A to the Anthony Declaration: Exhibits 1-9 cited in the Anthony Declaration, 9 pages, Aug. 8, 2012.
Appendix B to the Anthony Declaration: Ammons et al., "A Novel Alkylating Agent, Glufosfamide, Enhances the Activity of Gerncitabine In Vitro and In Vivo," Neoplasia 9(8): 625-633 (2007).
Appendix C to the Anthony Declaration: Chiorean et al., "A Phase 2 Trial of Glufosfamide in Combination with Gemcitabine in Chernotherapy-Naïve Pancreatic, Adenocarcinorna," American Journal of Clinical Oncology 33(2): 111-116 (2010).
Appendix D to the Anthony Declaration: Ciuleanu et al., "A Randomised Phase III Trial of Glufosfamide Comixired with Best Supportive Care in Metastatic Pancreatic; Adenocarcinoma Previously Treated with Gemcitabine," European Journal of Cancer 45: 1589-1596 (2009).
Declaration of Edwin Thomas dated Jul. 20, 2012 as filed on Aug. 8, 2012 in U.S. Appl. No. 10/588,409, now Patent No. 8,318,683, 4 pages.
Banting et al., "The Internal Secretion of the Pancreas," The Journal of Laboratory and Clinical Medicine 7(5):251-266 (1922).
Baur et al., "Transport of Hexoses across the Liver-Cell Membrane," European Journal of Biochemistry 74(2): 397-403 (1977).
Berger et al., "Decreased Expression of the Insulin-Responsive Glucose Transporter in Diabetes and Fasting," Nature 340(6228): 70-72 (1989).
Bourey et al., "Effects of Altered Glucose Homeostasis on Glucose Transporter Expression in Skeletal Muscle of the Rat," The Journal of Clinical Investigation 86(2): 542-547 (1990).
Briasoulis et al., "Glufosfamide Administered using a 1-Hour Infusion given as First-Line Treatment for Advanced Pancreatic Cancer. A Phase II Trial of the EORTC-New Drug Development Group," European Journal of Cancer 39(16): 2334-2340 (2003).
Fendrich et al., "Detection of Precursor Lesions of Pancreatic Adenocarcinoma in PET-CT in a Genetically Engineered Mouse Model of Pancreatic Cancer," Neoplasia 13(2): 180-186 (2011).
Garvey et al., "Pretranslational Suppression of an Insulin-Responsive Glucose Transporter in Rats with Diabetes Mellitus," Science 245(4913): 60-63 (1989).
Kahn et al., "Differential Regulation of Two Glucose Transporters in Adipose Cells from Diabetic and Insulin-Treated Diabetic Rats," The Journal of Clinical Investigation 84(2):404-411 (1989).
McCulloch et al., "GLUT2 (*SLC2A2*) is not the Principal Glucose Transporter in Human Pancreatic Beta Cells: Implications for Understanding Genetic Association Signals at this Locus," Molecular Genetics and Metabolism 104: 648-653 (2011).
Oka et al., "Increased Liver Glucose-Transporter Protein and mRNA in Streptozocin-Induced Diabetic Rats," Diabetes 39(4): 441-446 (1990).
Simpson et al., "Hormonal Regulation of Mammalian Glucose Transport," Annual Review of Biochemistry 55: 1059-1089 (1986).
Sivitz et al., "Regulation of Glucose Transporter Messenger RNA in Insulin- Deficient States," Nature 340(6228): 72-74 (1989).

(56) References Cited

OTHER PUBLICATIONS

Tal et al., "Expression and Function of GLUT-1 and GLUT-2 Glucose Transporter Isoforms in Cells of Cultured Rat Pancreatic Islets," The Journal of Biological Chemistry 267(24): 17241-17247 (1992).

Thorens et al., "Cloning and Functional Expression in Bacterial of a Novel Glucose Transporter Present in Liver, Intestine, Kidney, and Beta-Pancreatic Islet Cells," Cell 55(2): 281-290 (1988).

Williams et al., "Stereospecific Transport of Glucose in the Perfused Rat Liver," American Journal of Physiology 215(5): 1200-1209 (1968).

Yamamoto et al., "Liver and Muscle-Fat Type Glucose Transporter Gene Expression in Obese and Diabetic: Rats," Biochemical and Biophysical Research Communications 175(3): 995-1002 (1991).

\* cited by examiner

TREATMENT OF CANCER WITH GLUFOSFAMIDE IN PATIENTS NOT RECEIVING INSULIN THERAPY

CROSS-REFERENCE

This application claims priority to U.S. provisional application No. 60/991,660, filed 30 Nov. 2007, 60/952,686, filed 30 Jul. 2007, 60/915,882, filed 3 May 2007 and 60/910,403, filed 5 Apr. 2007, each of which is incorporated herein by reference.

FIELD OF THE INVENTION

The invention provides methods for treating cancer with glufosfamide administered in combination with glucose lowering drugs other than insulin and, optionally, with other anti-cancer therapies, such as surgery and radiation therapy. The invention relates to the fields of biomedicine, pharmacology, and molecular biology.

BACKGROUND OF THE INVENTION

Glufosfamide, also known as beta-D-glucosyl-ifosfamide mustard or glc-IPM, is a prodrug of an alkylating agent that has been used in the clinic as an investigational agent in the treatment of cancer. See U.S. Pat. Nos. 5,622,936 and 6,489,302 and PCT Publication Nos. WO 05/076888, WO 06/071955, WO 06/122227, and WO 07/035,961, each of which is incorporated herein by reference. In contrast to the alkylating agent prodrug ifosfamide, metabolism of glufosfamide does not release the toxic metabolite acrolein, and also produces less of the toxic metabolite chloroacetaldehyde. Glufosfamide was recently used in a Phase III clinical trial to determine if was effective in the treatment of pancreatic cancer; the trial did not meet its endpoints, although the data indicated that the drug was having an anti-cancer effect. There accordingly remains a need for new therapies for the treatment of cancer with glufosfamide. The present invention meets this need by providing novel combination therapies as summarized below and described in detail herein.

SUMMARY OF THE INVENTION

In one aspect, the present invention provides a method of treating cancer, said method comprising the steps of (i) determining whether a patient is receiving a glucose lowering drug other than insulin, and, if said patient is not receiving said drug, then administering to said patient a glucose lowering drug other than insulin, and then (ii) administering a therapeutically effective amount of glufosfamide to said patients in need of such treatment. In the course of treating patients, both those patients determined to already be under treatment with a glucose lowering drug other than insulin, and those newly receiving the glucose lowering drug other than insulin may be treated with glufosfamide. Accordingly, the glucose lowering drug can be administered prior to or contemporaneously with the administration of glufosfamide, and administration of the glucose lowering drug can continue after the administration of glufosfamide. In certain embodiments, the glucose lowering drug other than insulin is administered from at least 7 days to at least 1 day, at least 4 days to at least 2 days, and at least 3 days prior to the glufosfamide administration. In one embodiment, administration of the glucose lowering drug begins on the day glufosfamide therapy is initiated. In certain other embodiments, the glucose lowering drug other than insulin is administered from 3 days to 1 day, and up to 2 days after the glufosfamide administration. In certain other embodiments, the glucose lowering agent other than insulin is administered within a day of the glufosfamide administration.

In another aspect, the present invention provides a method of treating cancer comprising administering a therapeutically effective amount of glufosfamide in combination with a glucose lowering drug other than insulin to a patient in need of such treatment. In one embodiment, the patient is not suffering from diabetes mellitus, i.e., the patient is not a diabetic patient. In another embodiment, the patient is suffering from diabetes mellitus, i.e., the patient is a diabetic patient. In one embodiment, the patient does not have a glucose level that would indicate that administration of a glucose lowering drug is medically indicated. In one embodiment, the patient is receiving insulin, and insulin administration is stopped, and administration of a glucose lowering agent is initiated prior to the administration of glufosfamide. In one aspect of the invention if a patient identified as receiving insulin administration is stopped and the patient is then treated with glufosfamide.

In one embodiment, the glucose lowering drug other than insulin is selected from a sulfonylurea and a thiazolidinedione. In various embodiments, the glucose lowering drug is selected from the group consisting of glipizide, glibenclamide, glimepiride, gliclazide, and rosiglitazone, acetohexamide, chloropropamide, metformin, nateglinide, pioglitazone, repaglinide, tolazamide, and tolbutamide. In one embodiment the glucose lowering drug is a sulfonylurea.

A variety of cancers can be treated in accordance with the present methods. In one embodiment, the cancer treated is a primary pancreatic cancer. In another embodiment, the cancer is metastatic pancreatic cancer. In another embodiment, the cancer is gemcitabine resistant pancreatic cancer.

In one embodiment, the methods of the present invention are practiced in combination with other methods for treating cancer, including, for example, methods involving the administration of other anti cancer drugs, radiation, and/or surgery. A variety of anticancer drugs can be used in combination with the combination of glufosfamide and a glucose lowering drug other than insulin for the treatment of cancer as provided by the present invention. Illustrative anticancer drugs useful in the methods of the invention are described, for example, in the Physician's Desk Reference, the Merck Index, U.S. Pat. No. 6,979,675; US Pat. Pub. No. 2006/0276527; and PCT Pub. Nos. WO 06/057946 and WO 07/002931, each of which is incorporated herein by reference.

In another aspect, the present invention provides a method of treating cancer comprising administering a therapeutically effective amount of glufosfamide in combination with an IGF to a patient in need of such treatment. In one embodiment, the IGF is IGF-1. In another embodiment, the method further comprises administering another anti cancer drug and/or surgery and/or radiation therapy.

In another aspect, the present invention provides a method of treating cancer comprising administering a therapeutically effective amount of glufosfamide in combination with an IGF raising agent to a patient in need of such treatment; the IGF raising agent being an agent that can raise IGF levels when administered to the patient. In one embodiment, the method further comprises administering another anti cancer drug and/or or surgery and/or radiation therapy. In one embodiment the IGF raising agent is a sulfonylurea. In another embodiment the IGF raising agent excludes a sulfonylurea. Illustrative anticancer drugs useful in certain aspects of the invention are described, for example, in U.S. Pat. No. 6,979,675; US Pat.

Pub. No. 2006/0276527; PCT Pat. Pub. No. WO 06/57946; and PCT Pat. App. No. US06/015881, each of which is incorporated herein by reference.

In another aspect, the present invention provides a method of treating cancer comprising administering a therapeutically effective amount of glufosfamide in combination with a glycosidase to a patient in need of such treatment. In one embodiment, the glycosidase is a glucosidase. In another embodiment, the glucosidase is a β-glucosidase. In another embodiment, the glucosidase is a glucuronidase. In another embodiment, the glucosidase is a β-glucocerebrosidase. In another embodiment, the β-glucocerebrosidase is Cerezyme® (Imiglucerase, Genzyme).

In another aspect, the present invention provides a method of determining whether a cancer in a cancer patient is susceptible to treatment with glufosfamide, the method comprising the steps of:
(a) measuring the level of an in IGF in the cancer patient,
(b) comparing the level of the IGF measured with a predetermined level of the IGF, and
(c) determining that, if the level of the IGF measured is larger than the predetermined level of the IGF, the cancer is susceptible to treatment with glufosfamide. In one embodiment, the IGF is IGF-1.

In another aspect, the present invention provides a method of determining whether a cancer in a cancer patient is susceptible to treatment with glufosfamide, the method comprising the steps of:
(a) measuring the level of a glycosidase in the cancer patient,
(b) comparing the level of the glycosidase measured with a predetermined level of the glycosidase, and
(c) determining that, if the level of the glycosidase measured is larger than the predetermined level of the glycosidase, the cancer is susceptible to treatment with glufosfamide. In one embodiment, the glycosidase is a glucosidase. In one embodiment, the glucosidase is a disaccharidase. In another embodiment, the disaccharidase is lactase phlorizin hydrolase.

These and other aspects and embodiments of the present invention are described by the accompanying figures and the detailed description.

DETAILED DESCRIPTION OF THE INVENTION

This detailed description of the aspects and embodiments of the present invention is organized as follows: Section I provides definitions of terms used herein; Section II, in parts A and B, describes a clinical trial of glufosfamide for the treatment of gemcitabine resistant pancreatic cancer, including overall patient survival (part A), and the results obtained for a subset of diabetic patients receiving glucose lowering drugs other than insulin (part B); Section III, in parts A through D, describes the therapies provided by the present invention, including drug administration cycles (part A), illustrative treatment combinations (part B), cancers amenable to treatment (part C), and treatment of hyperproliferative diseases other than cancer (part D); and Section IV describes patient and in vivo treatment results that demonstrate the efficacy of the present methods. This detailed description is organized into sections only for the convenience of the reader, and disclosure found in any section is applicable to disclosure elsewhere in the specification.

I. DEFINITIONS

The following definitions are provided to assist the reader. Unless otherwise defined, all terms of art, notations, and other scientific or medical terms or terminology used herein are intended to have the meanings commonly understood by those of skill in the chemical and medical arts. In some cases, terms with commonly understood meanings are defined herein for clarity and/or for ready reference, and the inclusion of such definitions herein should not be construed as representing a substantial difference over the definition of the term as generally understood in the art.

"Administering" or "administration of" a drug to a patient (and grammatical equivalents of this phrase) refers to direct administration, which may be administration to a patient by a medical professional or may be self-administration, and/or indirect administration, such as the act of prescribing a drug. For example and without limitation, a physician who instructs a patient to self-administer a drug and/or provides a patient with a prescription for a drug is, for purposes of the present invention, "administering" the drug to the patient.

"Diabetes mellitus" refers to a group of metabolic diseases characterized by high serum glucose levels, which can result, for example, from defects in insulin secretion, action, or both.

A "diabetic patient" refers to a patient suffering from diabetes mellitus.

"Glucose lowering drugs" refer to drugs that are capable of reducing serum glucose levels in humans. Examples of glucose lowering drugs include sulfonylureas and thiazolidinediones. Other drugs useful as glucose lowering drugs include metformin, nateglinide, glipizide, glibenclamide, glimepiride, gliclazide, and rosiglitazone. Although one property of insulin is to lower glucose levels, as used in the description of the methods of the invention, "a glucose lowering drug" does not include insulin. Such drugs may also be referred to herein as "glucose lowering drugs other than insulin."

A "patient" refers to a mammal in need of treatment for cancer or, in some embodiments, for a hyperproliferative disease other than cancer. Generally, the patient is a human. In other embodiments of the invention, however, the patient is a non-human mammal, such as a non-human primate, a dog, cat, cow, horse, rabbit, pig, or the like. In other embodiments of the invention, the patient is an animal such as a mouse or rat, such as an animal commonly used in screening, characterizing, and evaluating drugs and therapies.

"Treatment" or "therapy" refers to a method for obtaining beneficial or desired results, including clinical results. For purposes of this invention, beneficial or desired clinical results include, but are not limited to, alleviation or amelioration of one or more symptoms, diminishment of extent of disease, stabilized (i.e., not worsening) state of disease, preventing spread of disease, delaying or slowing of disease progression, amelioration or palliation of the disease state, and remission (whether partial or total). "Treatment" can also mean prolonging survival as compared to expected survival in the absence of receiving treatment.

II. CLINICAL TRIAL INVESTIGATING THE TREATMENT OF GEMCITABINE RESISTANT PANCREATIC CANCER BY ADMINISTRATION OF GLUFOSFAMIDE

Glufosfamide is a prodrug of an alkylating agent useful in the treatment of cancer. A multi-center, randomized, open-label phase 3 clinical trial was conducted to evaluate the safety and efficacy of glufosfamide in treating gemcitabine resistant metastatic pancreatic cancer as measured by overall survival compared to BSC (best supportive care). Three hundred and three patients were randomized to the trial: 148 patients were randomized to the glufosfamide arm (n=148, Group 1) and 155 to BSC (n=155, Group 2).

A. Overall Survival

Patients in Group 1 were administered glufosfamide for up to 42 weeks. Glufosfamide was administered intravenously over 6 hours once every 3 weeks at 4500 mg/m$^2$ for up to 14 doses. This dosing schedule is shown in Table 1 below:

TABLE 1

|  | Glufosfamide | | |
| --- | --- | --- | --- |
| Week | 1 | 2 | 3 |
| Group 1 | Administered | — | — |
| Group 2 | — | — | — |

One-quarter of the dose was infused over 30 minutes and the remainder over the following five and one-half hours.

To assess the efficacy of glufosfamide treatment, patients in Group 1 and Group 2 were not administered any medication known to have antitumor effects other than glufosfamide, e.g., the patients were not administered any other chemotherapy or systemic cytotoxic/cytostatic agents. However, other appropriate supportive measures and concomitant medications not known to have antitumor effects, such as analgesics, antibiotics, transfusions, hematopoietic colony-stimulating factors (as therapy but not as prophylaxis), erythropoietin, and megestrol acetate for appetite stimulation were administered when appropriate.

Tumor assessment was performed at baseline and once every 6 weeks for the first 24 weeks and then once every 9 weeks. The primary efficacy indicator was the overall survival in Group 1 compared to that in Group 2.

Figure 1:
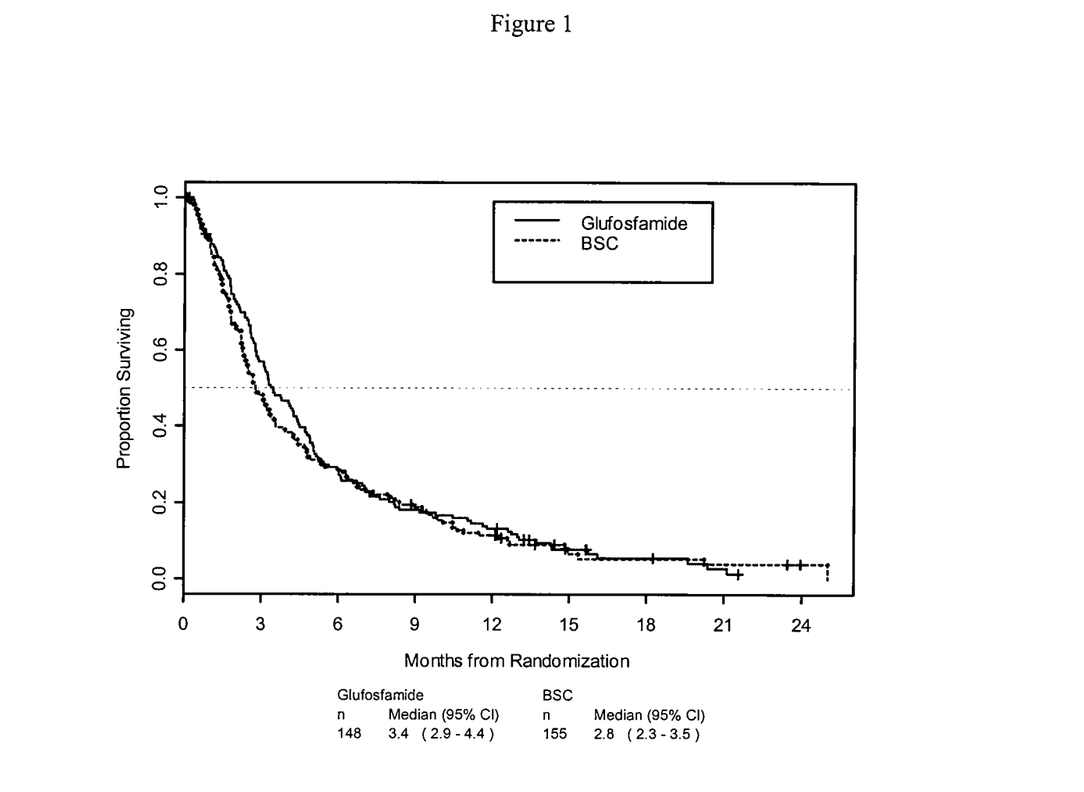
FIG. 1 shows comparative plots of survival over time for patients administered glufosfamide (Group 1) and patients administered best supportive care (BSC, Group 2).

The median overall survival was 105 days (95% confidence interval (CI); 87-133 days) in Group 1 and 84 days (95% CI; 71-106 days) in Group 2 (see FIG. 1). The relative risk for overall survival in Group 1 and Group 2 patients, determined from a proportional hazards model with Karnofsky Performance Status (KPS) as a stratification factor, was 0.848 (95% CI: 0.664-1.084), and the two-sided stratified log-rank p-value was 0.187.

Figure 2:
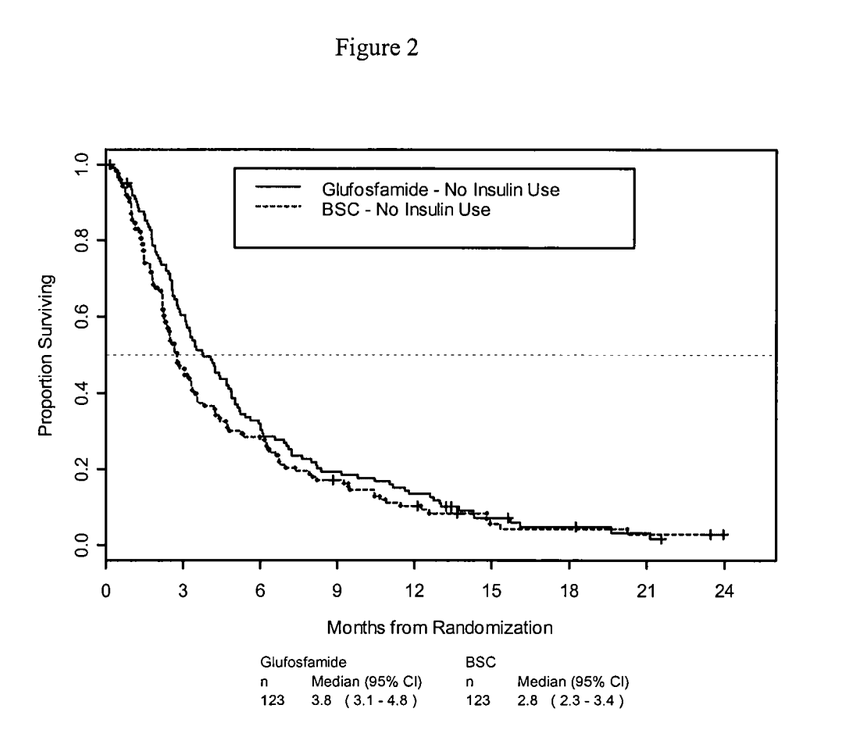
FIG. 2 shows comparative plots of survival over time for patients in Groups 1 and 2 who had not received insulin prior to initiation of glufosfamide therapy.

Patients (n=123) within Group 1 who were not administered insulin prior to the first administration of glufosfamide demonstrated a longer overall survival as compared to patients in Group 2 that were not administered insulin prior to their enrollment (n=123); the median overall survival within the Group 1 patients was 115 days (95% CI: 94-145 days) compared to 84 days (95% CI; 70-102 days) for those within Group 2 (see FIG. 2). The relative risk for overall survival in Group 1 and Group 2 patients, determined as above, was 0.761 (95% CI: 0.581-0.998), and the two-sided stratified log-rank p-value was 0.048.

While these results demonstrated that glufosfamide was effective in delaying disease progression and death in some patients, the trial did not meet its endpoints. The present invention arose from the discovery that certain patients responded to glufosfamide therapy much better than others and other patients responded less well than others and that those responses correlated with the co-administration of insulin or of a glucose-lowering drug other than insulin the patient received while undergoing glufosfamide therapy. Patients receiving insulin tended to experience no benefit or less benefit from the administration of glufosfamide and patients receiving a glucose lowering drug other than insulin tended to experience more benefit from the administration of glufosfamide than other patients not receiving such drugs.

B. Glufosfamide Treatment in Combination with Glucose Lowering Drugs

Seven diabetic patients (n=7) within Group 1 were treated with a glucose lowering drug (glipizide, glibenclamide, glimepiride, gliclazide, or rosiglitazone) but were not administered insulin prior to the first administration of glufosfamide. The median overall survival for these seven Group 1 patients was 418 days (95% CI; 85 days-643 days). In contrast, diabetic patients within Group 2 (n=14) who received various glucose lowering drugs other than insulin had a median overall survival of 73 days (95% CI; 45-102 days). The relative risk for overall survival in this subset of Group 1 and Group 2 patients, determined as above, was 0.24 (95% CI: 0.07-0.87), and the two-sided stratified log-rank p-value was 0.020. See FIG. 3. These results indicated that the benefits of glufosfamide therapy are greatly enhanced by the coadministration of a glucose lowering drug other than insulin. Accordingly, the present invention provides methods of treating cancer in patients by co-administering with glufosfamide a glucose lowering drug other than insulin, such as a sulfonylurea and a thiazolidinedione, to improve the effectiveness of glufosfamide therapy in the treatment of cancer.

III. THERAPEUTIC METHODS OF THE INVENTION

In one aspect, the present invention provides a method of treating a patient diagnosed with cancer, by 1) determining whether the patient is receiving a glucose lowering drug other than insulin, and,
2) if it is determined the patient is not receiving a glucose lowering drug other than insulin, then administering such a drug, and
3) administering a therapeutically effective amount of glufosfamide to the patient.

Thus a patient under prior treatment with a glucose lowering drug other than insulin is treated by administering a therapeutically effective amount of glufosfamide, and a patient not under prior treatment with a glucose lowering drug other than insulin is treated with such a glucose lowering drug and with a therapeutically effective amount of glufosfamide. The glucose lowering drug can be administered prior to and/or contemporaneously with and/or after the initiation of the administration of glufosfamide ("Glufos Day 1"). As used in this context, "contemporaneously" can mean the two drugs are administered on the same day, or on consecutive days, or within a week of one another. It will be understood that use of the word "or" in this context does not exclude combinations, such as administration the day before and the same day as glufosfamide administration.

In one approach the glucose lowering drug is administered as part of a treatment regimen contemporaneously with each of multiple administrations of glufosfamide (e.g, at least 2, 3, 4, 5, 6, 7, 8, 9, 10, 11, 12, 13 or 14 rounds of administration). In one approach the glucose lowering drug is administered as part of a treatment regimen contemporaneously with each administrations of glufosfamide.

In one approach the glucose lowering drug is administered at least once during each round of glufosfamide administration. For example, Table 1, above, shows a 3 week administration cycle. Thus in one embodiment the glucose lowering drug is administered at least once during each cycle of glufosfamide treatment (whether on a three-week cycle or a different cycle). More often the glufosfamide is given more than once during each cycle, such as at least 2, 3, 4, 5, 6, 7, 8, 9, 10, 11, 12, 13 or at least 14 times.

In one approach the glucose lowering drug is administered as part of a treatment regimen contemporaneously with each administrations of glufosfamide. For example, the glucose lowering drug may be given daily throughout the course of glufosfamide treatment, or daily at least through several cycles.

Again, it will be understood that description of certain administration schedules is not intended to be limiting, and that, for example, combinations of administration schedules described herein.

In one the glucose lowering drug is administered throughout approach the glucose lowering drug is administered as part of a treatment regimen contemporaneously with each of multiple administrations of glufosfamide (e.g, at least 2, 3, 4, 5, 6, 7, 8, 9, 10, 11, 12, 13 or 14 rounds of administration). In one approach the glucose lowering drug is administered as part of a treatment regimen contemporaneously with each administrations of glufosfamide.

When the glucose lowering drug ("GLD") is administered prior to Glufos Day 1, the GLD administration can begin at least 7 (Day -7), at least 6 (Day -6), at least 5 (Day -5), at least 4 (Day -4), at least 3 (Day -3), at least 2 (Day -2) or at least 1 (Day -1) day(s) prior to Glufos Day 1. Once initiated the GLD can be administered daily (including multiple doses in one same day) or less frequently. For illustration and not limitation, the GLD can be administered prior to Glufos Day 1 on Days -7, -5, -3, and -1; or Days -7, -6, -5, -4, and -3; or Days -4, -3, -2, and -1; or Days -4, -3, and -2. In various embodiments the GLD is administered for at least 1, at least 2, at least 3, at least 4, at least 5, at least 6 or at least 7 days during the seven-day period preceding initiation of glufosfamide treatment.

When the glucose lowering drug other than insulin is administered contemporaneously with the initiation of glufosfamide administration it is administered the same day glufosfamide is administered.

When the GLD is administered after the initiation of glufosfamide therapy it can be administered daily, on the same days glufosfamide is administered (e.g., once every 21 days if a three-week treatment cycle is used), one day before and/or one day after glufosfamide treatment, or according to another schedule. The GLD therapy can continue for the duration of glufosfamide treatment (e.g., up to 42 weeks, using the treatment cycle described above) or for a shorter period.

In one embodiment of the methods of the invention, the cancer patient is administered a glucose-lowering drug other than insulin at least during the period of time in which the patient is being administered glufosfamide. Often, in accordance with the methods of the invention, a glucose lowering drug other than insulin is administered throughout the period of glufosfamide administration and, usually, prior to initiation of glufosfamide treatment.

In another aspect, the present invention provides a method of treating cancer comprising administering a therapeutically effective amount of glufosfamide in combination with a glucose lowering drug other than insulin to a patient in need of such treatment. In one embodiment, the patient is not suffering from diabetes mellitus, i.e., the patient is not a diabetic patient, but the patient is administered a glucose lowering drug other than insulin, before, during, and/or after initiation of glufosfamide therapy. In another embodiment, the patient is suffering from diabetes mellitus, i.e., the patient is a diabetic patient, and, if the patient is receiving insulin, the insulin administration is stopped prior to administering glufosfamide.

In an aspect, the invention provides a method of treating cancer in a patient, said method comprising (i) determining if said patient is receiving a glucose lowering drug other than insulin; (ii) initiating administration of a glucose lowering drug other than insulin if said patient is not already receiving such drug; and (iii) administering a therapeutically effective amount of glufosfamide to said patient in need of cancer treatment.

In one embodiment, the patient has a normal glucose level at the time administration of the glucose lowering drug other than insulin is initiated.

In one embodiment, the glucose lowering drug is a sulfonylurea. In one embodiment, the glucose lowering drug is a thiazolidinedione. In other embodiments, the glucose lowering drug is selected from the group consisting of glipizide, glibenclamide, glimepiride, gliclazide, and rosiglitazone. Other glucose lowering drugs other than insulin useful in the methods of the present invention include, but are not limited to, acetohexamide, chloropropamide, metformin, nateglinide, pioglitazone, repaglinide, tolazamide, and tolbutamide.

In one aspect, the present invention provides a method of treating a patient diagnosed with cancer, by
1) determining whether the patient is receiving a glucose lowering drug other than insulin, and,
2) if it is determined the patient is not receiving a glucose lowering drug other than insulin, then administering such a drug, and
3) administering a therapeutically effective amount of glufosfamide to the patient.

In an embodiment the glucose lowering drug other than insulin is administered prior to the initiation of glufosfamide therapy. In an embodiment the glucose lowering drug other than insulin is administered contemporaneously with administration of glufosfamide therapy.

In one aspect, the present invention provides a method of treating a patient diagnosed with cancer, by
1) determining whether the patient is receiving a glucose lowering drug other than insulin, and,
2) if it is determined the patient is receiving a glucose lowering drug other than insulin, discontinuing therapy with the glucose lowering drug and initiating therapy with a different glucose lowering drug, and
3) administering a therapeutically effective amount of glufosfamide to the patient.

In an embodiment the glucose lowering drug other than insulin is administered prior to the initiation of glufosfamide therapy. In an embodiment the glucose lowering drug other than insulin is administered contemporaneously with administration of glufosfamide therapy.

In one aspect, the present invention provides a method of treating a patient diagnosed with cancer, by
1) determining whether the patient is receiving a glucose lowering drug other than insulin, and,
2) if it is determined the patient is receiving a glucose lowering drug other than insulin, discontinuing therapy with the glucose lowering drug and initiating therapy with a different glucose lowering drug, and 3) if it is determined the patient is receiving a glucose lowering drug other than insulin, discontinuing therapy with the glucose lowering drug and initiating therapy with a different glucose lowering drug, and 4) administering a therapeutically effective amount of glufosfamide to the patient.

In an embodiment the glucose lowering drug other than insulin is administered prior to the initiation of glufosfamide therapy. In an embodiment the glucose lowering drug other than insulin is administered contemporaneously with administration of glufosfamide therapy.

In one embodiment, if it is determined that a patient diagnosed with cancer is receiving insulin, then the insulin therapy is discontinued, prior to administration of glufosfamide. In one embodiment the glucose lowering drug other than insulin is administered to the patient in combination with glufosfamide. In one embodiment, the glucose lowering drug other than insulin is administered prior to the administration of glufosfamide.

The reference Guney et al., *Neuro. Endocrinol. Lett.*, 2002, 23(5-6):437-9, incorporated herein by reference, discloses that certain sulfonylurea-based glucose lowering drugs stimulate IGF-1 production. IGF-1, in turn, can upregulate the production of certain glucosidases. While the invention is not to be limited by any theory of mechanism of action, upregulated glucosidase levels in a cancer cell may lead to faster accumulation of and greater levels of isophosphoramide in cancer cells following glufosfamide administration.

In another aspect, the present invention provides a method of treating cancer comprising administering a therapeutically effective amount of glufosfamide in combination with an IGF raising agent to a patient in need of such treatment; the IGF raising agent being an agent that can raise IGF levels when administered to the patient. In one embodiment, the method further comprises administering another anti-cancer drug and/or surgery and/or radiation therapy. In one embodiment the IGF raising agent is a sulfonylurea. In another embodiment the IGF raising agent excludes a sulfonylurea. Illustrative anticancer drugs useful in certain aspects of the invention are described, for example, in U.S. Pat. No. 6,979,675; US Pat. Pub. No. 2006/0276527; PCT Pat. Pub. No. WO 06/57946; and PCT Pat. App. No. US06/015881, each of which is incorporated herein by reference.

Thus, in another aspect, the present invention provides a method of treating cancer comprising administering a therapeutically effective amount of glufosfamide in combination with a compound having IGF-1 activity (an "IGF") to a patient in need of such treatment. In one embodiment, the IGF is IGF-1. IGF-1 is available commercially as INCRELEX™ (Tercica, Brisbane, Calif.) and can be, for example and without limitation, administered at 0.04 to 0.12 mg/kg (40 to 120 μg/kg) twice daily by subcutaneous injection. See also, Dagogo-Jack et al., *Int. J. Obes. Relat. Metab. Disord.*, 1998, 22(11):1110-15, incorporated herein by reference. In another embodiment, the method further comprises administering another anti-cancer drug and/or surgery and/or radiation therapy. When additional anti-cancer agents are employed in the methods of the invention, they are typically administered at their approved doses and dosing frequency, or at lower doses or reduced frequency.

In another aspect, the present invention provides a method of treating cancer comprising administering a therapeutically effective amount of glufosfamide in combination with a glycosidase to a patient in need of such treatment. In one embodiment, the glycosidase is a glucosidase. In another embodiment, the glucosidase is a β-glucosidase. In another embodiment, the glucosidase is a glucuronidase. In another embodiment, the glucosidase is a β-glucocerebrosidase. In another embodiment, the β-glucocerebrosidase is Cerezyme® (Imiglucerase, Genzyme).

In another aspect, the present invention provides a method of treating cancer comprising administering a therapeutically effective amount of glufosfamide in combination with an agent that raises IGF-1 levels or activity ("an IGF raising agent") to a patient in need of such treatment. In one embodiment, the method further comprises administering another anti cancer drug and/or surgery and/or radiation therapy. In one embodiment the IGF raising agent is a sulfonylurea. In another embodiment the IGF raising agent is an agent other than a sulfonylurea.

In accordance with the methods of the invention, an IGF, an IGF raising agent, or a glycosidase administered in combination with glufosfamide or another anti-cancer drug can be administered in any amount that is therapeutically effective, and such amount will typically be the same as or less than the amounts of that drug that are routinely utilized clinically when the drug is not co-administered with an anti-cancer agent. A therapeutically effective amount of a glucosidase administered according to the present methods can be determined from the enzymatic activity of the glucosidase reported in literature and upon reading this disclosure in its entirely. A method for determining glucosidase activity is described for example in the reference Sun et al., *J. Chromatograpy B*, 2006, 832:224-30, incorporated herein by reference. The glucosidase Cerezyme® is administered by intravenous infusion over 1-2 h in the dosage range from 2.5 unit/kg of body weight 3 times a week to 60 unit/kg once every 2 weeks, product information for Cerezyme® available from Genzyme Corporation.

In another aspect, the present invention provides a method of determining whether a cancer in a cancer patient is susceptible to treatment with glufosfamide, the method comprising the steps of:

(a) measuring the level of an in IGF in the cancer patient, (b) comparing the level of the IGF measured with a predetermined level of the IGF, and (c) determining that, if the level of the IGF measured is larger than the predetermined level of the IGF, the cancer is susceptible to treatment with glufosfamide. In one embodiment, the IGF is IGF-1.

In another aspect, the present invention provides a method of determining whether a cancer in a cancer patient is susceptible to treatment with glufosfamide, the method comprising the steps of:

(a) measuring the level of a glycosidase in the cancer patient, (b) comparing the level of the glycosidase measured with a predetermined level of the glycosidase, and (c) determining that, if the level of the glycosidase measured is larger than the predetermined level of the glycosidase, the cancer is susceptible to treatment with glufosfamide. In one embodiment, the glycosidase is a glucosidase. In one embodiment, the glucosidase is a disaccharidase. In another embodiment, the disaccharidase is lactase phlorizin hydrolase.

In another aspect, the present invention provides a method of determining whether a cancer in a cancer patient is susceptible to treatment with glufosfamide, the method comprising the steps of (i) measuring the level of an IGF in the cancer patient, (ii) comparing the level of the IGF measured with a predetermined level of the IGF, and (iii) determining that, if the level of the IGF measured is larger than the predetermined level of the IGF, the cancer is susceptible to treatment with glufosfamide, and if the level is lower, then determining that the level should be increased prior to the administration of glufosfamide therapy. In one embodiment, the IGF is IGF-1. In one embodiment, the predetermined level of the IGF-1 is the level of IGF-1 found in normal humans. In another embodiment, the predetermined level of the IGF-1 is 200-450 ng/mL. See http://www.usdoctor.com/hgh.htm and Ho et al., *Clin. Endocrinol.*, 1994, 41(1):75-83, incorporated herein by reference. In another embodiment, the predetermined level of the IGF-1 is about 300-400 ng/mL. In various embodiments a predetermined level of about 200 ng/mL, about 300 ng/mL, about 400 ng/mL or about 450 ng/mL is used.

Various methods can be employed to determine the level of IGF in a patient including, but not limited to, radioimmunoassay by competitive protein binding, enzyme-linked immunoabsorbant assay, immunochemiluminescence assay, immunofunctional assay, kinase receptor activation assay, and free IGF-1 assay. See Clemmons et al., Pituitary, 2007, DOI 10.1007/s11102-007-0032-z, incorporated herein by reference.

A. Administration Cycles

Cancer chemotherapy treatment typically involves multiple "rounds" or "cycles" of drug administration, where each cycle comprises administration of the drug one or more times according to a specified schedule (e.g., daily; once per week for two or more weeks; multiple times a week either on consecutive days or non-consecutive days; once every cycle, which may be a day, week, or month, for example; multiple times every cycle [for example and without limitation every three weeks for three consecutive days], wherein each cycle ranges from 1 day to 1 week up to several weeks, such as 2, 3, 4, 5, 6, 7, or 8 weeks). For example and without limitation, chemotherapeutic drugs can be administered for from 1 to 8 cycles, or for more cycles (i.e., a longer time period).

As is understood in the art, treatment with anti-cancer therapeutic drugs can be suspended temporarily if toxicity is observed, or for the convenience of the patient, without departing from the scope of the invention, and then resumed.

In one embodiment of the invention, glufosfamide is administered for 1, 2, 3, 4, 5, 6, 7, 8, or more than 8 dosage cycles, and each cycle involves the administration by infusion of glufosfamide in the range of:

a) about 1.0 to about 8.0 g/m$^2$; about 1.0 to about 6.0 g/m$^2$; about 1.5 to about 4.5 g/m$^2$; about 4.5 to about 8.0 g/m$^2$; about 4.5 to about 6.0 g/m$^2$; or about 4.5 to about 5.0 g/m$^2$ or over an infusion period of 1-6 hours once every three weeks;

b) about 1.0 to about 3.0 g/m$^2$, about 1.5 to about 3.0 g/m$^2$ or about 1.5 to about 2.0 g/m$^2$ over an infusion period of 1-6 hours for three consecutive days (days 1, 2 and 3) every three weeks;

c) about 1.0 to about 2.0 g/m$^2$ or about 1.5 to about 2.0 g/m$^2$ over an infusion period of 1-6 hours once per week; or d) about 1.0 to about 8.0 g/m$^2$; about 1.0 to about 6.0 g/m$^2$; or about 1.5 to about 4.5 g/m$^2$ over an infusion period of 1-6 hours once every four weeks.

In one embodiment, glufosfamide is administered for 1, 2, 3, 4 or more than 4 dosage cycles, wherein each cycle is a seven-week cycle. In one embodiment, glufosfamide is administered for 1, 2, 3, 4, 5, 6, or more than 6 dosage cycles, wherein each cycle is a three-week cycle. In one embodiment, glufosfamide is administered for 1, 2, 3, 4, 5, 6, or more than 6 dosage cycles, wherein each cycle is a four-week cycle. In one embodiment, glufosfamide is administered weekly in the range of 1.0 to about 3.0 g/m$^2$, for example and without limitation on Days 1 and 8 of a 21 day cycle; on Days 1, 8, and 15 of a 28 day cycle; or Days 1, 8, and 15 of a 21 day cycle.

As used in this context, an "infusion period of 1-6 hours" includes without limitation, an infusion period of about 1, about 2, about 3, about 4, about 5, and about 6 hours.

In those embodiments of the invention in which an anti-cancer drug in addition to glufosfamide is co-administered with a glucose lowering drug other than insulin and glufosfamide, the cycles chosen for administration of the additional anti-cancer drug will typically be those commonly used for administering the anti-cancer drug when used alone or in combination with other agents.

B. Treatment Combinations

During chemotherapy treatment of cancer, two, three, or four anti-cancer drugs can be administered to a patient "in combination" by administering them as part of the same course of therapy. A course of therapy refers to the administration of combinations of drugs believed by the medical professional to work together additively, complementarily, synergistically, or otherwise to produce a more favorable outcome than that anticipated for administration of a single drug for the total number of cycles believed to provide efficacious treatment. A course of therapy can be for one or a few days, but, as discussed in the context of treatment cycles above, more often extends for several weeks or months.

When more than one drug (e.g., two drugs) is administered to a patient, as in the methods of the present invention, each drug can be administered according to its own schedule. It will be clear that administration of drugs, even those administered with different periodicity, can be coordinated so that both drugs are administered on the same day at least some of the time or, alternatively, so the drugs are administered on consecutive days at least some of the time.

When two or more anti-cancer drugs are administered in combination, as in certain embodiments of the methods of the present invention, a variety of schedules can be used. In one case, for example and without limitation, Drug 1 is first administered prior to administration of Drug 2, and treatment with Drug 1 is continued throughout the course of administration of Drug 2; alternatively, Drug 1 is administered after the initiation or completion of Drug 2 therapy; alternatively, Drug 1 is first administered contemporaneously with the initiation of the other cancer therapy. As used in this context, "contemporaneously" means the two drugs are administered on the same day or on consecutive days or within a week of one another.

The present invention contemplates that the drugs used in combination in the methods of the invention can be co-formulated for administration in combination or can be administered as separate compositions Similarly, the present invention contemplates that certain drugs combinations will be administered simultaneously (for drugs administered by infusion), other drug combinations will be co-administered in separate compositions, other drug combinations will be administered at different times on the same day, or on consecutive days, or according to other schedules. As clear from this context, "co-administration" means administration in the same course of therapy.

In accordance with the methods of the invention, a glucose lowering drug administered in combination with glufosfamide can be administered in any amount that is therapeutically effective, and such amount will typically be the same as, but could be less or more than, the amount of that drug that is routinely utilized clinically when the drug is administered for its previously approved indications. In similar fashion, the anti-cancer agent other than glufosfamide administered according to the present methods is likewise typically administered in the amounts used for its previously approved anti-cancer therapeutic indications (although lower amounts, reduced frequency may be employed in some instances). Thus, the therapeutically effective amount of a drug that can be administered is known to physicians and provided, for example and without limitation, in the product descriptions found in the most recent editions of the PHYSICIANS' DESK REFERENCE, Medical Economics Company, Inc., Oradell, N.J.; and Goodman & Gilman's THE PHARMACOLOGICAL BASIS OF THERAPEUTICS", McGraw-Hill, New York; and/or are available from the Federal Drug Administration and/or are discussed in the medical literature.

For illustration and not limitation, the administration of glufosfamide and various other anti-cancer drugs for treatment of cancer is found in U.S. Patent Application No. 61/027,768, filed 11 Feb. 2008; 60/991,660, filed 30 Nov. 2007; 60/952,686, filed 30 Jul. 2007; 60/915,882, filed 3 May 2007; and 60/910,403, filed 5 Apr. 2007, and PCT Pub. Nos. WO 05/076888, WO 06/071955, WO 06/122227, and WO 07/035,961, each of which is incorporated herein by reference. The administration and dosing schedules described in these publications and applications are suitable for use in the methods of the present invention.

C. Cancers Treatable in Accordance with the Methods of the Invention

In one embodiment, the present invention provides methods for treating pancreatic cancer. In another embodiment, the cancer treated is selected from a primary pancreatic cancer, metastatic pancreatic cancer, and gemcitabine resistant pancreatic cancer (primary and metastatic). Chemotherapy-resistant pancreatic cancers (see, e.g., Araneo et al., 2003, *Cancer Invest.* 21:489-96; Kozuch et al., 2001, *The Oncologist* 6:488-95; Noble and Goa, 1997, *Drugs* 54: 447-72N; Stephens et al., 1998, *Oncol. Nurs. Forum* 25:87-93; Burris and Storniolo, 1997, *Eur. J. Cancer* 33: Suppl 1:S18-22; Rothenberg et al., 1996, *Ann. Oncol.* 7:347-53, each of which is incorporated herein by reference) can be treated using the methods disclosed herein. In one embodiment of the invention, serum carbohydrate 19-9 is used as a marker for evaluating the response to such glufosfamide therapy in pancreatic cancer (Ziske et al., 2003, *Br. J. Cancer,* 89:1413-17, incorporated herein by reference).

In various embodiments, the methods of the present invention are employed to treat a cancer selected from the group consisting of breast cancer, colorectal cancer, gall bladder cancer, non-Hodgkin's lymphoma, kidney cancer, liver cancer, lung cancer, ovarian cancer, pancreatic cancer, sarcoma, and stomach cancer.

In one embodiment of the present invention, glufosfamide and a glucose lowering drug other than insulin are co-administered to a subject in need of treatment for breast cancer. Breast cancer is commonly treated by various combinations of surgery, radiation therapy, chemotherapy, and hormone therapy. In accordance with the methods of the invention, glufosfamide is administered alone, or in combination with gemcitabine, or in combination with another anti-cancer drug for the treatment of breast cancer, and a glucose lowering drug other than insulin is co-administered with glufosfamide.

In one embodiment of the present invention, glufosfamide and a glucose lowering drug other than insulin are co-administered to a subject in need of treatment for colorectal cancer or metastatic colorectal cancer. Colorectal cancer or metastatic colorectal cancer is currently treated by radiation therapy, surgery, and/or chemotherapy (e.g., administration of fluorouracil). In one embodiment, glufosfamide is the only anti-cancer agent administered to treat colorectal cancer; in another embodiment, glufosfamide is co-administered with another anti-cancer agent, such as gemcitabine, to treat colorectal cancer. In another embodiment, glufosfamide and bevacizumab are administered in combination with a glucose lowering drug other than insulin to a subject in need of treatment for colorectal cancer; optionally, gemcitabine or fluorouracil is also co-administered.

In one embodiment of the present invention, glufosfamide and a glucose lowering drug are co-administered as a second-line therapy for non-Hodgkins lymphoma after CHOP (cyclophosphamide, adriamycin, vincristine, and prednisone) therapy has failed.

In one embodiment of the present invention, glufosfamide and a glucose lowering drug are co-administered to a subject in need of treatment for ovarian cancer. Optionally, gemcitabine is also co-administered. In one embodiment, glufosfamide and a glucose lowering drug are co-administered, and again, gemcitabine can be optionally co-administered, as a second line therapy in the treatment of ovarian cancer, optionally in combination with an approved second line therapy after failure on cis/carboplatin and/or a taxane or other first line therapy. In another aspect, glufosfamide and a glucose lowering drug are co-administered as a first line therapy in the treatment of ovarian cancer, optionally in combination with gemcitabine and/or cis/carboplatin and/or a taxane and/or another first line therapy.

In another embodiment of the invention, glufosfamide and a glucose lowering drug are co-administered as a first- or second-line therapy to treat a PET-positive sarcoma. A "PET-positive" sarcoma is a sarcoma detectable by positron emission tomography. In one embodiment, glufosfamide and a glucose lowering drug are co-administered as a second line therapy in the treatment of a sarcoma either alone or in combination with another approved second line therapy after treatment failure on doxorubicin or failure on another first line therapy. In another embodiment, glufosfamide and a glucose lowering drug are co-administered as a first line therapy in the treatment of a sarcoma in combination with doxorubicin or in combination with another approved first line therapy.

In one embodiment of the present invention, glufosfamide and a glucose lowering drug are co-administered as a second line therapy in small-cell lung cancer (SCLC) optionally in combination with gemcitabine and optionally with another approved second line therapy after first line failure on carboplatin or cisplatin, VP16, and/or a taxane. In another aspect, glufosfamide and a glucose lowering drug are co-administered alone or in combination with gemcitabine as a first line therapy in the treatment of SCLC, optionally in combination with carboplatin or cisplatin, VP16, and/or a taxane or other approved first line therapy.

In general, the methods of the present invention can be used for treatment of any cancer. In various embodiments, the cancer treated is selected from the group consisting of cancer of the adrenal gland, bone, brain, breast, bronchi, colon and/or rectum, gallbladder, head and neck, kidneys, larynx, liver, lung, neural tissue, pancreas, prostate, parathyroid, skin, stomach, and thyroid. In other embodiments, the cancer treated is selected from the group consisting of acute and chronic lymphocytic and granulocytic tumors, adenocarcinoma, adenoma, basal cell carcinoma, cervical dysplasia and in situ carcinoma, Ewing's sarcoma, epidermoid carcinomas, giant cell tumor, glioblastoma multiforma, hairy-cell tumor, intestinal ganglioneuroma, hyperplastic corneal nerve tumor, islet cell carcinoma, Kaposi's sarcoma, leiomyoma, leukemias, lymphomas, malignant carcinoid, malignant melanomas, malignant hypercalcemia, marfanoid habitus tumor, medullary carcinoma, metastatic skin carcinoma, mucosal neuroma, myeloma, mycosis fungoides, neuroblastoma, osteo sarcoma, osteogenic and other sarcoma, ovarian tumor, pheochromocytoma, polycythermia vera, primary brain tumor, small-cell lung tumor, squamous cell carcinoma of both ulcerating and papillary type, hyperplasia, seminoma, soft tissue sarcoma, retinoblastoma, rhabdomyosarcoma, renal cell tumor, small cell lung cancer, topical skin lesion, veticulum cell sarcoma, and Wilm's tumor.

D. Treatment of Hyperproliferative Diseases Other Than Cancer

In another aspect, the methods of the present invention are practiced to treat a disease other than cancer that is characterized by cellular hyperproliferation (e.g., an abnormally increased rate or amount of cellular proliferation). In various embodiments, the hyperproliferative disease is selected from the group consisting of allergic angiitis and granulomatosis (Churg-Strauss disease), asbestosis, asthma, atrophic gastritis, benign prostatic hyperplasia, bullous pemphigoid, coeliac disease, chronic bronchitis and chronic obstructive airway disease, chronic sinusitis, Crohn's disease, demyelinating neuropathies, dermatomyositis, eczema including atopic dermatitis, eustachean tube diseases, giant cell arteritis, graft rejection, hypersensitivity pneumonitis, hypersensitivity vasculitis (Henoch-Schonlein purpura), irritant dermatitis, inflammatory hemolytic anemia, inflammatory neutropenia, inflammatory bowel disease, Kawasaki's disease, multiple sclerosis, myocarditis, myositis, nasal polyps, nasolacrimal duct diseases, neoplastic vasculitis, pancreatitis, pemphigus vulgaris, primary glomerulonephritis, psoriasis, periodontal disease, polycystic kidney disease, polyarteritis nodosa, polyangitis overlap syndrome, primary sclerosing cholangitis, rheumatoid arthritis, serum sickness, surgical adhesions, stenosis or restenosis, scleritis, scleroderma, strictures of bile ducts, strictures (of duodenum, small bowel, and colon), silicosis and other forms of pneumoconiosis, type I diabetes, ulcerative colitis, ulcerative proctitis, vasculitis associated with connective tissue disorders, vasculitis associated with congenital deficiencies of the complement system, vasculitis of the central nervous system, and Wegener's granulomatosis.

In one embodiment, the hyperproliferative disease treated is psoriasis, a disease characterized by the cellular hyperproliferation of keratinocytes which builds up on the skin to form elevated, scaly lesions. In another embodiment, the hyperproliferative disease treated is multiple sclerosis, a disease characterized by progressive demyelination in the brain. In another embodiment, the hyperproliferative diseases treated is rheumatoid arthritis, a multi-system, chronic, relapsing, inflammatory disease that can lead to destruction and ankylosis of the joints affected by the disease.

The invention, having been described in summary and in detail, is illustrated but not limited by the Examples below, which demonstrates the efficacy of the administration of glufosfamide in combination with a glucose lowering drug other than insulin to treat cancer.

IV. EXAMPLES

Example 1

Figure 3:
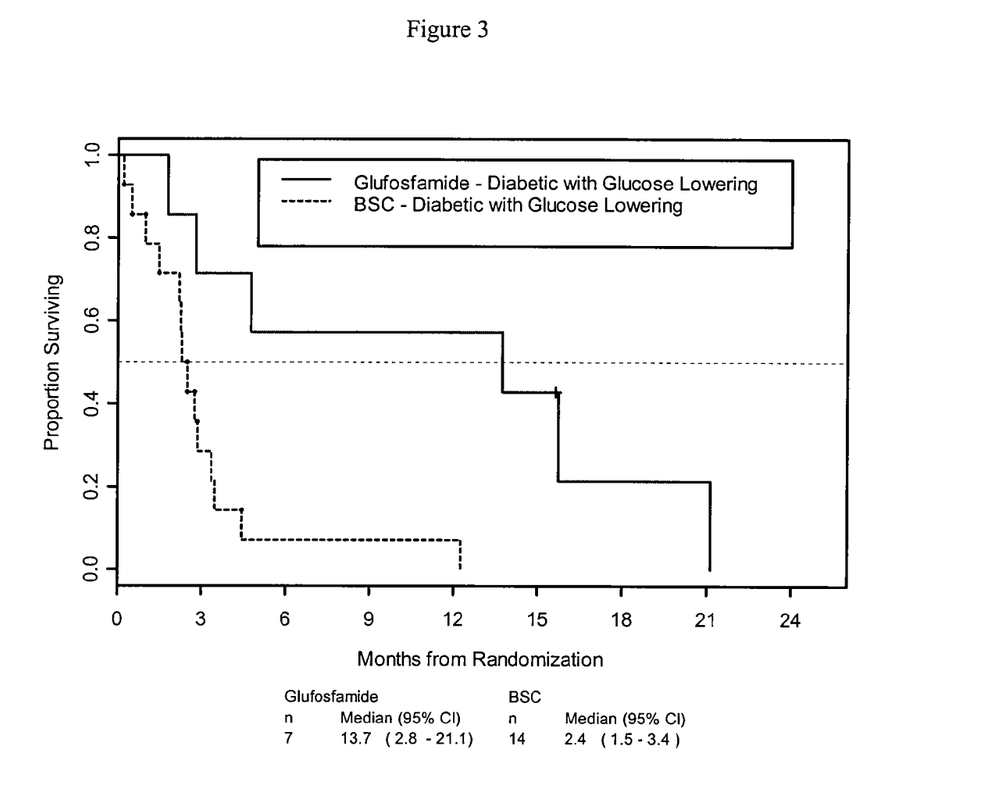
FIG. 3 shows comparative plots of patient survival over time in months for patients in Groups 1 and 2 who received a glucose lowering drug other than insulin during glufosfamide therapy.

Glufosfamide Treatment of Patients Receiving Glucose Lowering Drugs Other Than Insulin Seven diabetic patients (Group 1A) having gemcitabine resistant pancreatic cancer were treated with glufosfamide for 2-11 cycles in combination with various glucose lowering drugs (GLDs) other than insulin (see Table 2 below). Glufosfamide was administered intravenously over 6 hours, once every 3 weeks, at 4500 mg/m$^2$. The GLD was administered orally, once every day or qd, 738-139 days prior to the first glufosfamide administration; except that, the GLD was administered to patient no. 6 three times daily or tid. Fourteen diabetic patients (Group 2A) who did not receive GLDs and glufosfamide, received BSC. Tumor assessment was performed at baseline and once every 6 weeks for the first 24 weeks and then once every 9 weeks. Efficacy outcomes were evaluated based on comparing the overall median survival in Group 1A with that in Group 2A. The median overall survival in the Group 1A patients was 418 days (95% CI; 85 days-643 days) compared to 84 days (95% CI; 45 days-102 days) for those in group 2A (FIG. 3). The results demonstrate that glufosfamide administered in combination with a glucose lowering drug other than insulin is effective in treatment of gemcitabine resistant pancreatic cancer in diabetic patients.

TABLE 2

| Patient I.D. No. | GLD administered | GLD administered for days prior to first Glufosfamide administration | Amount of GLD administered (mg) | Glufosfamide administration cycles (4500 mg/m$^2$ over a period of 6 hours once every 3 weeks) | Actual overall survival |
|---|---|---|---|---|---|
| 1 | Glipizide | 738 | 5 | 11 | 418 |
| 2 | Glibenclamide | 462 | 5 | 2 | 85 |
| 3 | Rosiglitazone maleate | 453 | 8 | 2 | 479 |
| 4 | Glimepiride | 154 | 2 | 2 | 54 |
| 5 | Gliclazide | 139 | 40 | 2 | 145 |
| 6 | Glibenclamide | 308 | 1 tablet | 14 | 643 |
| 7 | Gliclazide | 657 | 90 | 4 | 476+ |

Example 2

Co-Administration of Glufosfamide and Glimepiride

This example demonstrates the efficacy of glufosfamide administered in combination with a glucose lowering drug, glimepiride, for the treatment of cancer. A total of sixty male NCr nu/nu mice, 5-6 weeks old, were used in the study. Original breeding pairs were purchased from Taconic, Germantown, N.Y. Test animals were bred and maintained in a HEPA filtered environment for the experiment. Cages, food and bedding were autoclaved. The animal diets were obtained from PMI Nutrition International Inc. (Brentwood, Mo.).

RFP expression vector: The pDsRed-2 vector was purchased from Clontech (Palo Alto, Calif.). The vector expresses enhanced RFP and the neomycin resistance gene on the same bicistronic message that contains an internal ribosome entry site.

RFP vector production: PT67, an NIH3T3-derived packaging cell line, expressing the 10 A1 viral envelope, was purchased from Clontech. PT67 cells were cultured in DMEM supplemented with 10% fetal bovine serum. For vector production, packaging cells (PT67), at 70% confluence, were incubated with a precipitated mixture of N-[1-(2,3-dioleoyloxyl)propyl]-N,N,N-trimethylammoniummethyl sulfate reagent and saturating amounts of pDsRed-2 plasmid for 18 h. Fresh medium was replenished at this time. The cells were examined by fluorescence microscopy 48 h post-transfection. For selection, the cells were cultured in the presence of 200-1000 μg/ml G418 for 7 days.

RFP gene transduction of MiaPaCa-2 cells: For RFP gene transduction, 20% confluent MiaPaCa-2 cells (ATCC, Rockville, Md.) were incubated with a 1:1 precipitated mixture of retroviral supernatants of PT67 cells and RPMI 1640 for 72 h. Fresh medium was replenished at this time. MiaPaCa-2 cells were harvested by trypsin-EDTA 72 h posttransduction and subcultured at a ratio of 1:15 into selective medium that contained 200 μg/ml G418. The level of G418 was increased to 1000 μg/ml stepwise. The brightest MiaPaCa-2 cell clones expressing RFP were selected, combined, and then amplified and transferred by conventional culture methods.

Subcutaneous Xenografts: Tumor stocks were made by subcutaneously injecting MiaPaCa-2-RFP cells at a concentration of $5 \times 10^6$ cells/200 μl into the flank of nude mice. see e.g., Bouvet et al. Cancer Res., 2002, 62, 1534-40 incorporated herein by reference. The strong RFP expression of tumors grown in the subcutis of mice was confirmed before harvest. The tumor tissues harvested from s.c growth in nude mice were inspected, and any grossly necrotic or suspected necrotic or non-RFP tumor tissues were removed. Tumor tissues were subsequently cut into small fragments of approximately 2 mm$^3$.

Surgical Orthotopic Implantation (SOI): The animals were transplanted by surgical orthotopic implantation (SOI) using the MiaPaCa-2-RFP tumor fragments harvested from the stock animals. The animals were anesthetized with isoflurane and the surgical area was sterilized using iodine and alcohol. An incision approximately 1.5 cm long was made in the left upper abdomen of the nude mouse using a pair of surgical scissors. The pancreas was exposed, and then two pieces of the MiaPaCa-2-RFP tumor fragments of 2 mm$^3$ were transplanted to the mouse pancreas with 8-0 surgical sutures (nylon) after the capsule of the transplantation site had been stripped. The abdomen was closed with 6-0 surgical sutures (silk). All procedures of the operation described above were performed with a 7× magnification microscope (Olympus) under HEPA filtered laminar flow hoods.

Study animals: The orthotopically-transplanted animals used for the study were divided into 6 groups 1 day after SOI. Groups for each of the cohort conditions were randomly chosen. Treatment: Treatments were started on day 1 after SOI. Table 3 shows the treatment schedule.

TABLE 3

| Group | Agents | Dose (mg/kg) | Dosing Schedule | Route | Number of Mice |
|---|---|---|---|---|---|
| 1 | Untreated Control | — | — | — | 10 |
| 2 | Glufosfamide | 50 | qd × 7 | i.v. | 10 |
| 3 | Glemiperide + Glufosfamide | 0.2 + 50 | qd × 14 + qd × 7 | p.o. + i.v. | 10 |
| 4 | Glemiperide + Glufosfamide | 1.0 + 50 | qd × 14 + qd × 7 | p.o. + i.v. | 10 |
| 5 | Glemiperide + Glufosfamide | 12 + 50 | qd × 14 + qd × 7 | p.o. + i.v. | 10 |
| 6 | Glemiperide | 12 | qd × 14 | p.o | 10 |

Primary tumor size and body weight measurement: Primary tumor sizes and body weights were measured weekly using an electronic caliper and an electronic scale. Primary tumor sizes were estimated by measuring the perpendicular minor dimension (W) and major dimension (L). Approximate tumor volume was calculated by the formula $(W^2 \times L) \times \frac{1}{2}$.

Fluorescence optical tumor imaging (FOTI): The FluorVivo imaging system (INDEC Biosystems, Santa Clara, Calif.) was used for whole body and open imaging. Whole body optical imaging of GFP-expressing tumors was performed once a week after GFP-visible tumors were established. At necropsy, open imaging was acquired for each animal.

Study endpoint: The study was ended when the last animal died on Aug. 15, 2007. Test animals were opened and imaged to visualize metastasis. The primary tumor was excised and weighed using an electronic balance.

Statistical methods used in efficacy evaluation: Tumor volumes and tumor weights were compared using the Student's t-test with an $\alpha = 0.05$. Metastatic frequency of all groups were analyzed with Fisher's exact test with an $\alpha = 0.05$. Comparison of animal survival time between each treatment group and untreated control was analyzed using the Log-rank analysis with an $\alpha = 0.05$.

Figure 4:
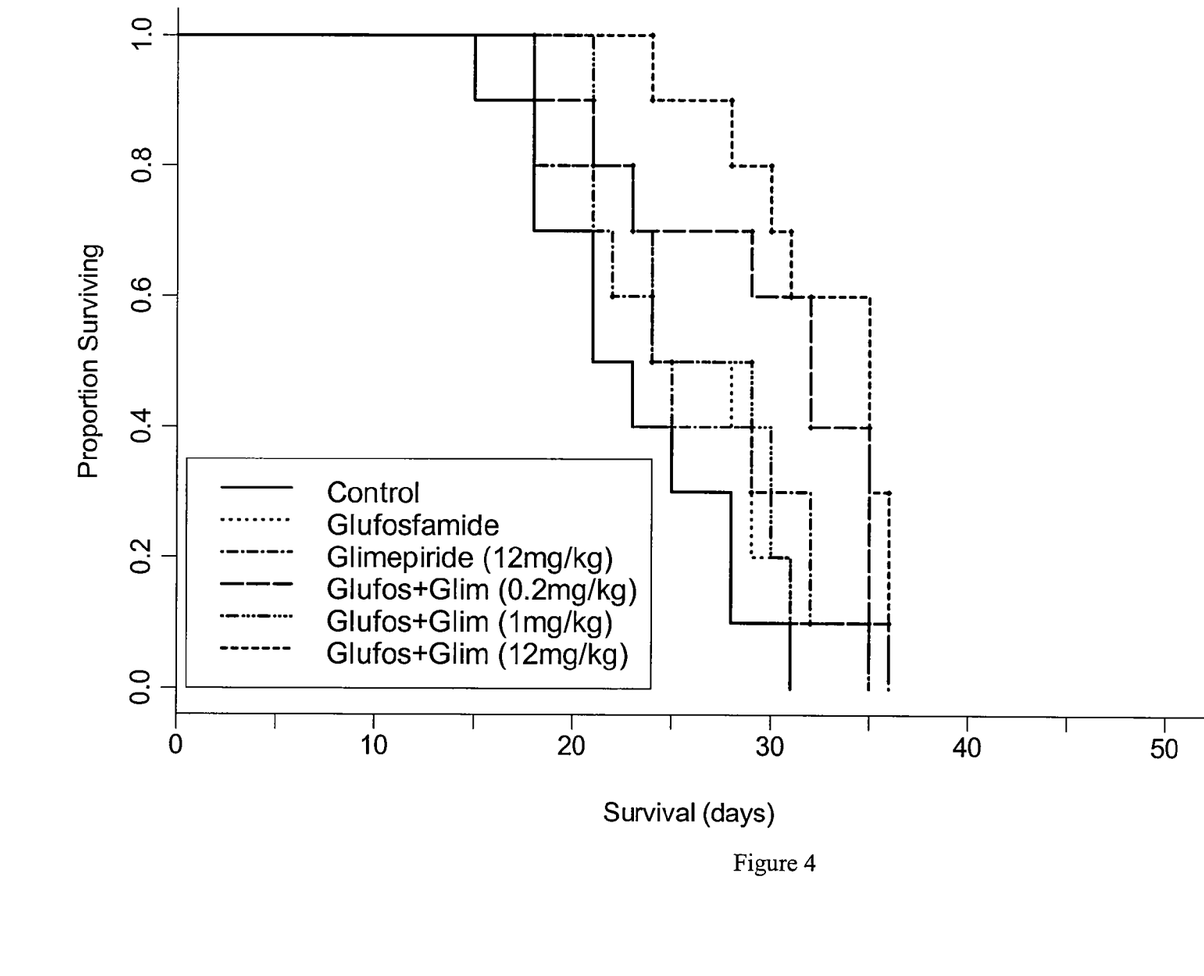
FIG. 4 shows in vivo survival benefits of co-administration of glufosfamide and the glucose lowering drug glimepiride in a murine cancer model.

The survival improvement is graphically shown in FIG. 4 and demonstrates that when administered in combination with glimepiride (12 mg/kg), glufosfamide (50 mg/kg) was more effective in extending survival compared to glufosfamide administered alone. Median overall survival was 35 days (log rank p-value<0.01) for glufosfamide administered in combination with glimepiride (12 mg/kg), compared to 26 days for treatment with glufosfamide alone.

While the present invention has been described with reference to the specific embodiments thereof, it should be understood by those skilled in the art that various changes can be made and equivalents can be substituted without departing from the scope of the invention. In addition, many modifications can be made to adapt a particular situation, material, composition of matter, process, process step or steps, to achieve the benefits provided by the present invention without departing from the scope of the present invention. All such modifications are intended to be within the scope of the claims appended hereto.

All publications and patent documents cited herein are incorporated herein by reference as if each such publication or document was specifically and individually indicated to be incorporated herein by reference. Citation of publications and patent documents is not intended as an indication that any such document is pertinent prior art, nor does it constitute any admission as to the contents or date of the same.

We claim:
1. A method of treating cancer in a patient, comprising the steps of:
   (i) determining whether the patient is receiving insulin therapy, and
   (ii) administering a therapeutically effective amount of glufosfamide to said patient only if it is determined that the patient is not receiving insulin therapy.

2. The method of claim 1, wherein said cancer is primary pancreatic cancer and/or gemcitabine resistant pancreatic cancer.

3. A method of treating cancer in a group of cancer patients, comprising the steps of:
   (i) identifying patients in the group who are not receiving insulin therapy; and then (ii) administering a therapeutically effective amount of glufosfamide only to patients in the group who are identified as not receiving insulin therapy; thereby obtaining:
   a first plurality of cancer patients within said group still receiving insulin therapy and not receiving glufosfamide; and
   a second plurality of cancer patients within said group receiving glufosfamide and not receiving insulin therapy.

4. The method of claim 1 or claim 3, further comprising administering to at least some of the cancer patients receiving glufosfamide therapy a blood glucose lowering drug other than insulin.

5. The method of claim 4, wherein at least some of the patients treated with the blood glucose lowering drug have a normal glucose level at the time administration of the blood glucose lowering drug is initiated.

6. The method of claim 4, wherein the blood glucose lowering drug is selected from sulfonylureas and thiazolidinediones.

7. The method of claim 4, wherein the blood glucose lowering drug is selected from glipizide, glibenclamide, glimepiride, gliclazide, and rosiglitazone.

8. The method of claim 4, wherein the blood glucose lowering drug is selected from acetohexamide, chloropropamide, metformin, nateglinide, pioglitazone, repaglinide, tolazamide, and tolbutamide.

9. The method of claim 1 or claim 3, wherein the cancer is primary pancreatic cancer.

10. The method of claim 1 or claim 3, wherein the cancer is chemotherapy resistant pancreatic cancer.

* * * * *